(12) United States Patent
Nelson et al.

(10) Patent No.: US 8,973,441 B1
(45) Date of Patent: Mar. 10, 2015

(54) ULTRASONIC METHOD TO VERIFY THE INTERFERENCE FIT OF FASTENERS

(71) Applicant: The Boeing Company, Chicago, IL (US)

(72) Inventors: Karl E. Nelson, Shoreline, WA (US); Gary E. Georgeson, Federal Way, WA (US); Paul S. Rutherford, Renton, WA (US); Mark McKenna, Bethel, VT (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/047,925

(22) Filed: Oct. 7, 2013

Related U.S. Application Data (62) Division of application No. 12/579,710, filed on Oct. 15, 2009, now Pat. No. 8,578,778.

(51) Int. Cl.
*G01N 29/04* (2006.01)
(52) U.S. Cl.
CPC .................................. *G01N 29/043* (2013.01)
USPC ............................................. 73/602; 73/627
(58) Field of Classification Search
USPC .................... 73/602, 598, 627, 761
See application file for complete search history.

(56) References Cited

U.S. PATENT DOCUMENTS

| | | | |
|---|---|---|---|
| 4,602,511 A | 7/1986 | Hold | |
| 4,846,001 A | 7/1989 | Kibblewhite | |
| 6,116,094 A * | 9/2000 | Andersson | 73/761 |
| 7,644,627 B2 * | 1/2010 | Kibblewhite et al. | 73/761 |
| 7,730,784 B2 * | 6/2010 | Georgeson et al. | 73/579 |
| 7,946,179 B2 * | 5/2011 | Kibblewhite et al. | 73/761 |
| 8,037,772 B2 * | 10/2011 | Kibblewhite et al. | 73/761 |
| 8,671,761 B2 * | 3/2014 | Zagrai et al. | 73/598 |
| 8,683,869 B2 * | 4/2014 | Herley et al. | 73/761 |
| 2006/0137463 A1 | 6/2006 | Nassar | |
| 2009/0031811 A1 | 2/2009 | Georgeson | |

FOREIGN PATENT DOCUMENTS

JP 2001099817 A 4/2001

OTHER PUBLICATIONS

PCT International Search Report Apr. 27, 2011.

* cited by examiner

*Primary Examiner* — J M Saint Surin
(74) *Attorney, Agent, or Firm* — Toler Law Group, PC (57) ABSTRACT

Embodiments of techniques and technologies to verify the interference fit of fasteners are disclosed. In one embodiment, a transducer is positioned to transmit a shear ultrasonic signal through a region of a fastener which is subject to stress when the fastener experiences an interference fit. The shear ultrasonic signal is transmitted through a region of the fastener subject to the stress. As the transmitted ultrasonic signal encounters the region, it is mode converted corresponding to a degree of interference which the fastener is experiencing. A return ultrasonic signal from the fastener is received with the transducer. From the return ultrasonic signal, a processor determines the degree of interference fit which the fastener is experience and outputs an indication of the same.

20 Claims, 10 Drawing Sheets

ULTRASONIC METHOD TO VERIFY THE INTERFERENCE FIT OF FASTENERS

RELATED APPLICATIONS

This application is a divisional of U.S. patent application Ser. No. 12/579,710 to Nelson, et al., entitled ULTRASONIC METHOD TO VERIFY THE INTERFERENCE FIT OF FASTENERS, filed Oct. 15, 2009, the disclosure of which is incorporated herein by reference in its entirety.

TECHNICAL FIELD

The present disclosure teaches ultrasonic (US) measurement techniques, and more specifically, methods for ultrasonically measuring and verifying an interference fit of fasteners (IFF).

BACKGROUND

Recent estimations indicate that, on the average, various aircraft in the U.S. commercial aircraft fleet encounter lightning discharges about once each year. The aircraft generally encounters the lightning discharge when flying through a charged portion of a cloud. In such cases, the discharge generally attaches to the aircraft and extends outwardly from the aircraft. While the discharge is occurring, it generally moves from the nose of the aircraft and onto a plurality of skin panel portions of the aircraft as the aircraft moves through the charged region. The discharge may also attach to wing tips and/or edges of wing control surfaces (e.g., ailerons) during the discharge. The discharge then generally leaves the aircraft structure through the empennage. Since commercial aircraft include electronic equipment such as navigational computers and communications equipment that may be degraded by a lightning discharge, commercial aircraft comply with a comprehensive set of certification procedures in order to verify that the aircraft is sufficiently protected from the effects of a lightning discharge.

Meanwhile, today's aircraft are being designed and built with greater percentages of composite material. Although composites possess high strength to weight ratios and may have better mechanical and fatigue properties than traditional aluminum alloys, they are less electrically conductive, and offer somewhat less electromagnetic shielding than the metallic materials which they replace, causing somewhat less current dissipation from aircraft. Without a conductive path, arcing and stored voltage (capacitance) can occur that might degrade affected portions of the aircraft structure. For example, lightning may attach to a fastener and then flow though the fastener into a sub-structure below the surface (or skin) of the aircraft. Thus, techniques are implemented to provide conductive paths from portions of these aircraft including the fasteners.

Techniques to improve an airframe's tolerance of electrical charges, particularly when the electrical charges attach to aircraft fasteners, have utility and may improve the economy and/or safety of air transit.

SUMMARY

Embodiments of techniques and technologies to verify the interference fit of fasteners are disclosed. Such techniques and technologies may be used to inspect and verify an interference fit between an electrically-conductive fastener and an electrically-conductive layer of a Lightning Strike Protection (LSP) system of a structure, including a fiber-reinforced composite structure. Techniques in accordance with the present disclosure may advantageously ensure that an electrically-conductive path exists between the fastener and the LSP system so that an electrical charge may be conducted through the structure, thereby reducing or eliminating degradation that might otherwise occur to the structure. Moreover, such inspections can be done with the fastener in place and without having to measure the dimensions of every fastener and fastener hole intended for an interference fit.

Embodiments provide methods of determining a degree of an interference fit experienced by a fastener. These methods include positioning a transducer to transmit an ultrasonic shear wave signal through a region of the fastener which is subject to stress when the fastener experiences an interference fit. The methods also include transmitting the US shear wave signal through a region of the fastener subject to the stress. While not wishing to be held to the following theory, it is believed that as the transmitted ultrasonic shear wave travels through the region it changes in mode at the interference boundaries to a degree corresponding with the degree of interference which the fastener is experiencing. Moreover, the methods include receiving, from the fastener, the reflected ultrasonic signal with the transducer. The reflected ultrasonic signal is processed to determine the degree of interference fit which the fastener is experiencing and outputs an indication of the same. In some embodiments, the degree of the interference fit is determined by examining an amplitude/energy of the longitudinal wave and shear wave components of the return ultrasonic signal. In some embodiments, the determination is made by comparing the amplitude/energy of the longitudinal wave components and amplitude/energy of the shear wave component of the reflected ultrasonic signal. Furthermore, the indication of the degree of the interference fit can be a measurable indication for use in a graphical user interface.

In some embodiments, the interference fit is between the fastener, sleeve, and a composite material. In the alternative, or in addition, the reflected wave is from the end surface of a shank of the fastener. Furthermore, the transducer can be aligned with the fastener and applied thereto with a selected force during the transmitting and receiving of the ultrasonic signals. The alignment of the transducer and the fastener, as well as the selected force, can be based on a configuration of the fastener. Embodiments also provide computer readable storage medium which store computer executable instructions which cause a processor to perform methods such as the foregoing when executed thereby.

Embodiments provide systems for determining a degree of an interference fit experienced by a fastener. These systems include an ultrasonic transducer, a processor, and a memory in communication with one another. The memory stores computer readable instructions which when executed by the processor cause the processor to perform methods such as those describe above. In addition, the systems can include a display including a graphical user interface for displaying the degree of the interference fit. Moreover, the systems can include a method for aligning the ultrasonic transducer and the fastener, and for applying the ultrasonic transducer to the fastener with a selected force. Moreover, the alignment of the ultrasonic transducer and the fastener, as well as the force with which the ultrasonic transducer is applied to the fastener are system parameters which are controllable variables. Systems of some embodiments include a rail on which the ultrasonic transducer can be mounted in such a fashion that it can move along the rail between fasteners.

The features, functions, and advantages can be achieved independently in various embodiments of the present disclosure or may be combined in yet other embodiments.

BRIEF DESCRIPTION OF DRAWINGS

Embodiments of techniques in accordance with the present disclosure are described in detail below with reference to the following drawings. In the drawings, the left-most digit(s) of a reference number identifies the drawing in which the reference number first appears. The use of the same reference numbers in different drawings indicates similar or identical items or features.

DETAILED DESCRIPTION

Techniques and technologies to verify the interference fit of fasteners are disclosed herein. Many specific details of certain embodiments of the disclosure are set forth in the following description and in FIGS. 1 through 8 to provide a thorough understanding of such embodiments. One skilled in the art, however, will understand that the present disclosure may have additional embodiments, or that the present disclosure may be practiced without several of the details described in the following description.

This document discloses systems for determining the interference fit between fasteners and the materials in which they are installed. Additionally, this document discloses methods for doing the same. In some systems and methods, the degree of the interference fit is determined by transmitting a shear wave ultrasonic signal into the fastener and analyzing a mode-converted signal returned from the fastener. In some embodiments, the energy of a shear component and the energy of a longitudinal component of the mode-converted return signal are compared to determine the degree of the interference fit. In some embodiments, one or both amplitudes are considered in determining the degree of the interference fit.

Figure 1:
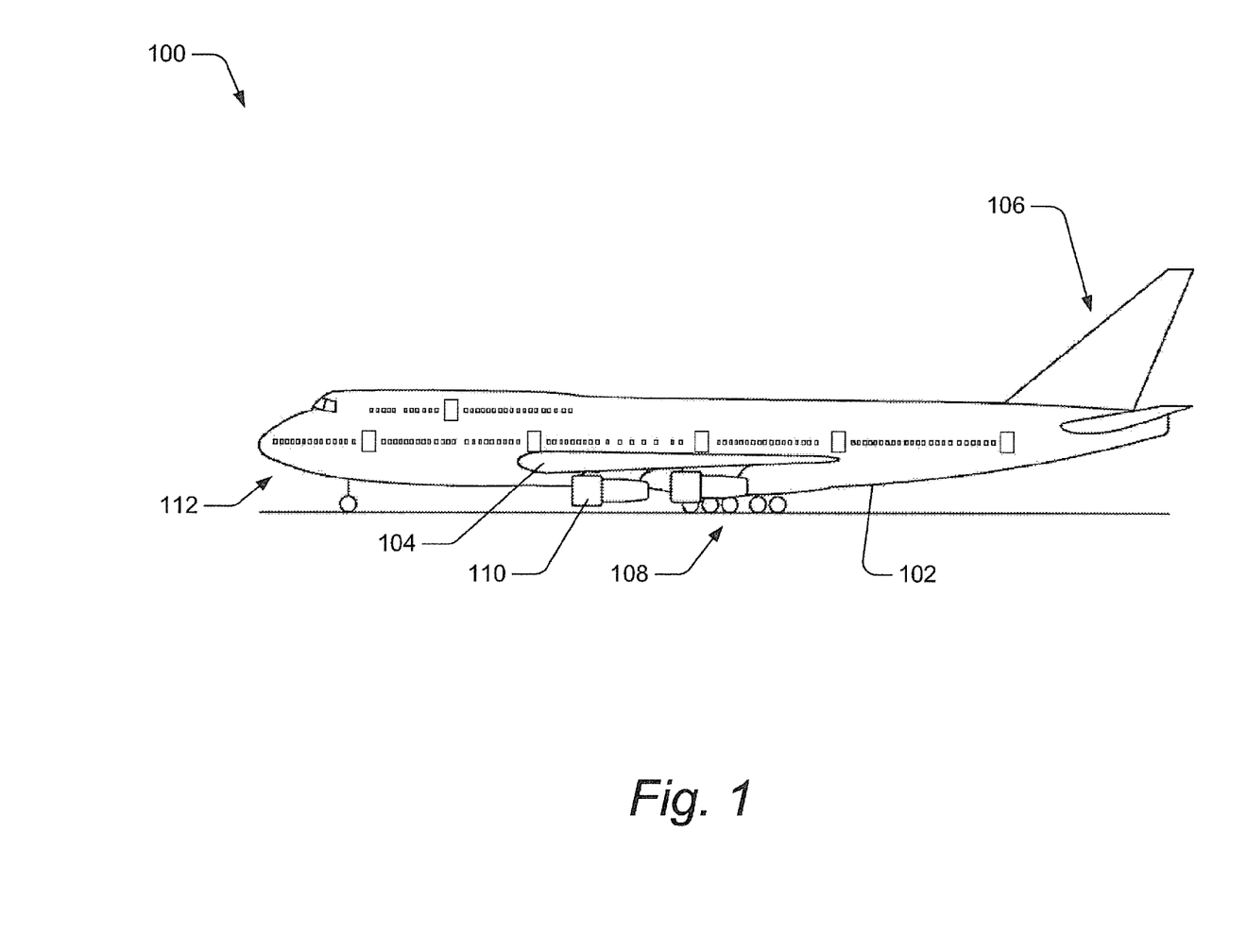
FIG. 1 is a side elevation view of an aircraft having interference fit fasteners verified in accordance with an embodiment of the disclosure.

FIG. 1 is a side elevation view of an aircraft 100 having interference fit fasteners verified in accordance with embodiments of the disclosure. One may appreciate that fasteners may be employed in a wide variety of locations, including the fuselage 102, wings 104, and empennage 106 of the aircraft 100. For example, the aircraft 100 may include many fasteners throughout the skin of the aircraft in accordance with an embodiment of the disclosure. In alternate embodiments, interference fit fasteners may be verified on other types of structures, vehicles, and platforms, such as motor vehicles, aircraft, maritime vessels, or spacecraft, or other suitable applications.

In this embodiment, the aircraft 100 includes a fuselage 102 including wing assemblies 104, a tail assembly 106, and a landing assembly 108. The aircraft 100 further includes one or more propulsion units 110, a control system 112 (not visible), and a host of other systems and subsystems that enable proper operation of the aircraft 100. One should appreciate that fasteners may be employed in any suitable portion of the aircraft 100, such as in a fuselage 102, wing assemblies 104, tail assembly 106, and any other suitable areas of the aircraft 100. In general, the various components and subsystems of the aircraft 100 may be of known construction and, for the sake of brevity, will not be described in detail herein.

Although the aircraft 100 shown in FIG. 1 is generally representative of a commercial passenger aircraft, including, for example, the 737, 747, 757, 767, 777, and 787 models commercially available from The Boeing Company of Chicago, Ill., the inventive apparatus and methods disclosed herein may also be employed in the assembly of virtually any other type of aircraft. More specifically, the teachings of the present disclosure may be applied to the manufacture and assembly of other passenger aircraft, fighter aircraft, cargo aircraft, rotary aircraft, and any other types of manned or unmanned aircraft, including those described, for example, in The Illustrated Encyclopedia of Military Aircraft by Enzo Angelucci, published by Book Sales Publishers, September 2001, and in Jane's All the World's Aircraft published by Jane's Information Group of Coulsdon, Surrey, United Kingdom, which texts are incorporated herein by reference.

Aircraft employ lightning strike protection (LSP) systems to protect the aircraft from degradation when it encounters lightning or otherwise undergoes an electrical charge. One approach is to incorporate a layer of conductive metal in the aircraft skin to evenly distribute electrical energy across a large surface area, and thus avoid concentrations of energy that might cause degradation of part of the aircraft. Often, fasteners that connect the aircraft skin to internal structures are protected from electrical charges by recessing the fasteners below the conductive layer within the skin of the aircraft. The fasteners are typically covered with a non-conductive material to further conceal the fasteners from electrical charges. Despite these precautions, electrical charges may occasionally attach themselves to a fastener and flow down the fastener shaft. In such an instance, it is desirable to effectively draw the electrical energy through the aircraft skin and other structures (for instance aircraft spars) in an efficient manner, and thus avoid heating and/or degradation to the fastener or surrounding material. In order for the electrical energy to be drawn from the fastener, the fastener advantageously has an interference fit with the surrounding material.

The interference fit of a fastener relates to a measure of closeness of the fit between the fastener shank, the fastener sleeve component, and the surrounding material forming a fastener hold. For example, the fastener hole may be drilled though the material at a diameter of 0.495 in. for a fastener shank/sleeve system with 0.500 in. diameter, thus creating a positive interference fit of 0.005 in. In such an instance, the fastener may be inserted into the hole by compressing the surrounding material in a direction perpendicular to the axis of the fastener shank.

While not intending to be bound by theory, it is believed that microscopic gaps typically exist between the fastener shank and the fastener hole. These gaps cause the current flow between the fastener shank and the material to be focused at the points where contact is made. By providing an interference fit, and thus compressing the surrounding material with the fastener shank, it is believed that the microscopic gaps are minimized resulting in increased electrical contact area and thus increased conductive properties between the fastener and the surrounding material. Increased conductivity reduces or eliminates any negative effect of electrical charge attaching to the fastener because the associated electrical energy may be dispersed into the skin or spar if the interference fit of the fastener is within a design threshold range.

As disclosed previously, aircraft are increasingly being constructed using composite materials, yet still encounter electrical charge on occasion. Generally, composite materials include fibers embedded in an epoxy or other substrate. While both the fibers and the substrate can be conductive, it sometimes happens that one or the other of these materials has better conductivity than the other. For instance, the carbon fibers of a carbon/epoxy composite can be expected to conduct electricity better than the epoxy substrate. Where the fastener is interference fit in a composite material, the interference fit helps bring the one or more components of the composite material into electrical contact with the fastener thereby improving the dissipation of electrical charge from the fastener. Accordingly, employing an interference fit between a fastener and a composite material increases the charge dissipation characteristics of the resulting assembly.

To ensure that interference fit is in conformance with design requirements, whether in a traditional, metallic structure or in a composite structure, methods to verify interference fits are desirable. For example, aircraft manufacturing variables can impede consistent fits between the fastener and the fastener hole. The sources of such inconsistencies include operator error, out-of-round conditions, slightly oversized/undersized drill bits, dull drill bits, undersized/oversized fasteners, etc. Methods are needed to confirm the degree of interference fits after the fasteners are installed, and in some cases, after extended use of aircraft to ensure that the interference fits remain within the design threshold ranges. U.S. patent application Ser. No. 11/833,826 entitled "Ultrasonic Method to Verify the Interference Fit of Fasteners," by Georgeson et al, and filed on Aug. 3, 2007 discloses methods and systems for determining the interference fits of fasteners and is incorporated herein as if set forth in full.

Figure 2:
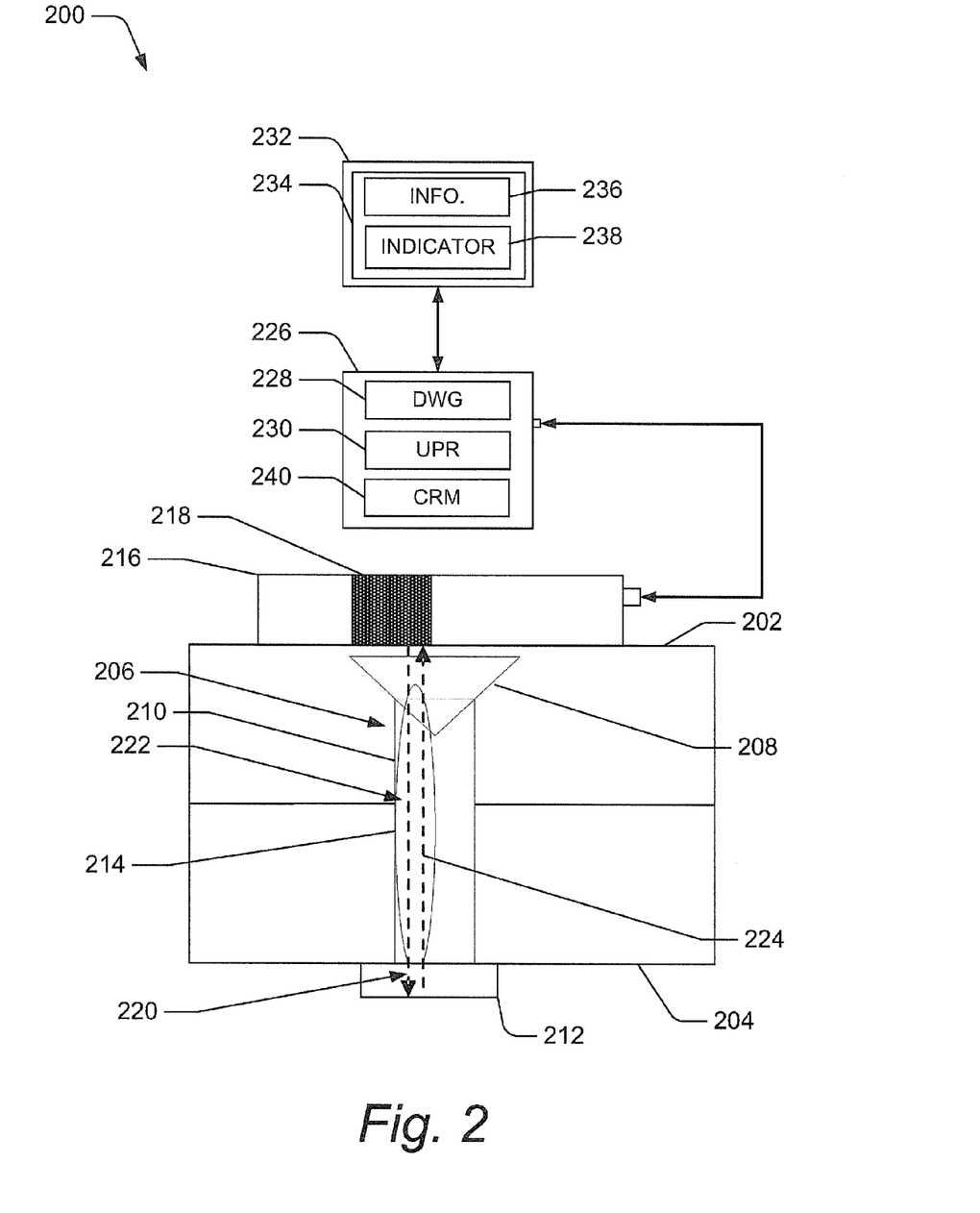
FIG. 2 is a cross-sectional view of an apparatus configured to verify an interference fit of a fastener in accordance with an embodiment of the disclosure.

FIG. 2 is a cross-sectional view of an apparatus configured to verify an interference fit of a fastener in accordance with an embodiment of the disclosure. A system 200 includes a first material 202 and a second material 204 securely coupled by a fastener 206 (including a head 208, a shank 210, and a nut 212) disposed through a fastener hole 214. Tightening the nut 212 on the shank 210 causes the fastener head 208 and the nut 212 to exert compressive forces on the first and second materials 202 and 204. In addition, the fastener shank 210 may create radial stresses in the first material 202 and the second material 204 when the system 200 includes an interference fit (wherein the unstressed fastener hole 214 has a smaller diameter than the diameter of the unstressed shank 210). The radial stresses in the first and second materials 202 and 204 may be highest at the interface between the fastener 206 and the materials 202 and 204, and typically reduces in magnitude as the distance from the fastener 206 increases. In reaction to the radial stress exerted on the first material 202 and the second material 204 by the fastener 206, the first material 202 and the second material 204 exert compressive stresses on the fastener 206 directed radially into the shank 210. These compressive stresses on the shank 210 might not be the same as each other and might vary across the surface of the shank 210 (as well as within the shank 210).

Detection and measurement of the compressive stresses arising from the interference fit may provide information about the interference fit, and thus allow measurement of it to determine if it is in conformance with a design range. Furthermore, information regarding the interference fit (or lack thereof) might indicate the degree to which the fastener installation will provide current dissipation into the conductive component(s) of the surrounding material. For instance, in the embodiment shown in FIG. 2, either one or both of the first and second materials 202 and 204 may be electrically conductive, may include an electrically-conductive layer of a Lightning Strike Protection (LSP) system, and/or, have a conductive component (for instance, carbon fibers) therein.

With continued reference to FIG. 2, the system 200 includes a fastener interference fit (IFF) probe 216. The IFF probe 216 includes an ultrasonic testing transducer 218. In some embodiments, the frequency between about 1 MHz to about 10 MHz and can be about 5 MHz. The shear wave transducer 218 produces ultrasonic signals 220 composed of numerous individually pulsed ultrasonic shear waves traveling substantially parallel to the axis of the fastener shank 210. As the ultrasonic signals 220 travel along the shaft, they encounter regions 222 in the shank 210 subject to the compressive stress exerted by the materials 202 and 204 on the shank 210 when the fastener 206 experiences an interference fit. The encounter with one or more of the regions 222 causes a mode conversion of the shear waves of the transmitted ultrasonic signal 220 to longitudinal waves in correspondence with the degree of the interference fit between the shank 210 and the materials 202 and 204. After, or while, passing through the regions 222, the transmitted ultrasonic signal 220 encounters the distal end of the fastener 206 whereupon it reflects (at least partially) back toward the shear wave transducer 218.

From the distal end of the fastener 206, a return ultrasonic signal 224 therefore travels back along the length of the fastener 206 generally in parallel to the axis of the fastener 206 and toward the shear wave transducer 218. As a result, the return ultrasonic signal 224 may encounter the same, or additional, regions 222 subject to the compressive stress arising from the interference fit. Thus, the return ultrasonic signal 224 may be further mode-converted to longitudinal waves in correspondence with the degree of the interference fit between the fastener 206 and the materials 202 and 204. As a result, the return ultrasonic signal 224 includes a mode-converted component characterized by longitudinal waves and a non-mode converted component characterized by shear waves.

More specifically, it has been found that the amplitude/energy of the longitudinal component of the return ultrasonic signal 224 indicates the degree of the interference fit between the fastener 206 and the materials 202 and 204. It has also been found that the amplitude/energy of the shear component of the return ultrasonic signal 224 also indicates the degree of the interference fit although in inverse proportion thereto. Furthermore, the product and ratio of the amplitudes of the shear and of the longitudinal components (or vice versa) of the return ultrasonic signal 224 have also been found to indicate the degree of the interference fit between the fastener 206 and the materials 202 and 204.

In some embodiments and with continuing reference to FIG. 1, the IFF probe 216 is in communication with a controller 226. The controller 226 may include a dynamic wave generator (DWG) 228 and an ultrasonic pulse receiver (UPR) 230 having signal analysis capabilities, however other configurations are contemplated. The dynamic wave generator 228 may provide wave generation information to the shear wave transducer 218. Furthermore, the ultrasonic pulse receiver 230 may receive signals from the shear wave transducer 218 indicative of the return ultrasonic signal 224. Therefore, the return ultrasonic signal 224 may be analyzed to determine information about the interference fit between the fastener 206 and the materials 202 and 204. For example, the controller 226 may be a computer, server, or other computing device including one or more processors operably connected to storage media storing modules to perform the techniques disclosed herein when executed by the processor, such as the functions performed by the dynamic wave generator 228 and the ultrasonic pulse receiver 230.

Furthermore, the controller 226 may communicate with a display 232 on which it displays a graphic user interface 234. The graphic user interface 234 can include information 236 regarding the fastener 206, the materials 202 and 204, and the system 200 (for instance, the degree of interference called for by the design of the particular installation for the fastener 206). In addition, or in the alternative, the graphic user interface 234 can include an indicator 238 for displaying an indication of the degree of the interference fit determined to exist by the controller 226. For instance, the indicator 238 could include a numeric read out of the degree of the interference fit, an analog indication of the same, a go/no-go indication for the fastener 206, or a graphical representation of the wave types. Thus, the indicator 238 can indicate whether the fastener 206 will provide current dissipation into the surrounding materials 202 or 204. Moreover, the controller 226 can include (or be in communication with) a tangible computer readable medium 240 or a memory device for storing computer readable instructions which when executed by the controller (or a processor) cause the controller 226 to perform the methods and/or implement (all or a portion of) the systems disclosed herein.

Figure 3:
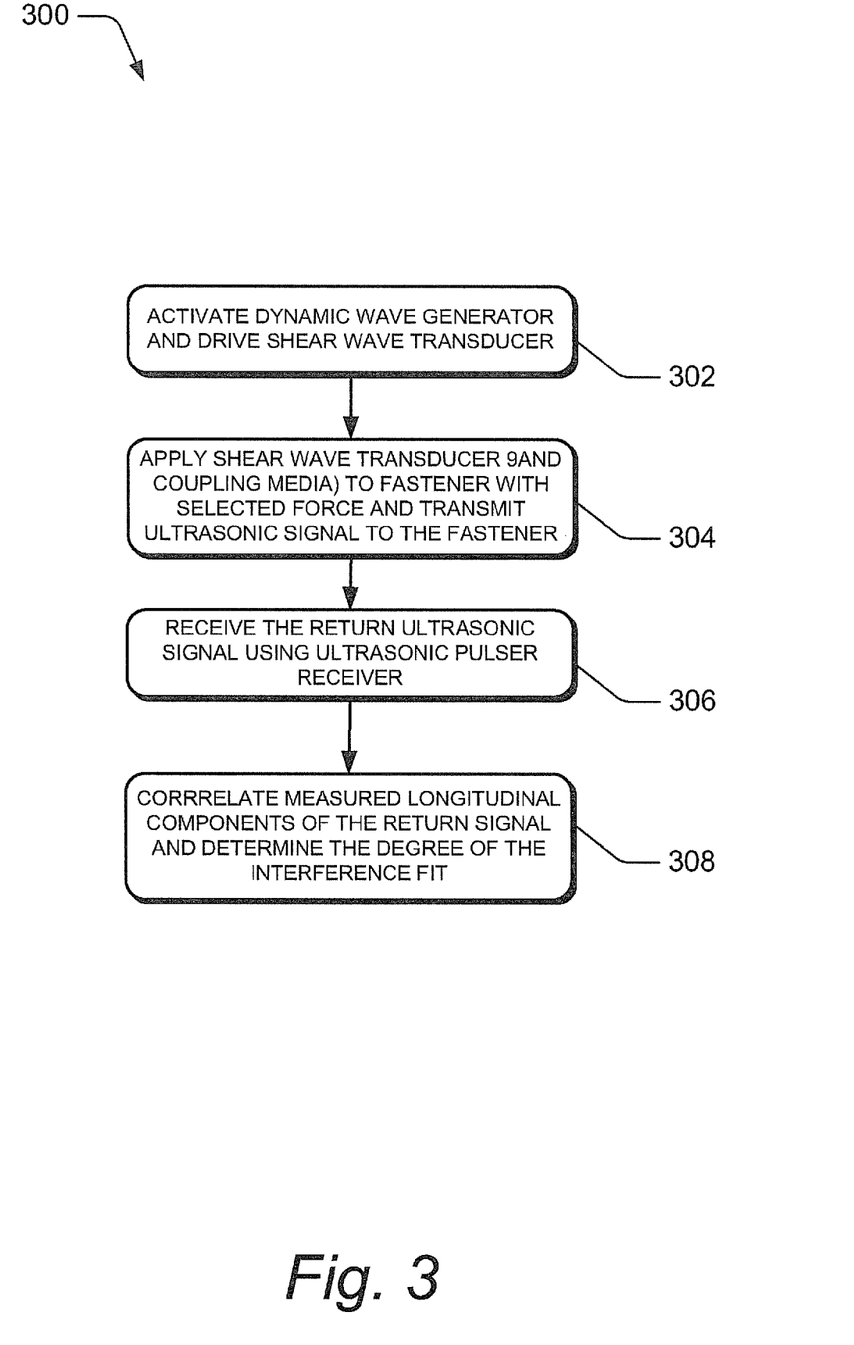
FIG. 3 is a flow diagram of a process for verifying the interference fit of a fastener in accordance with an embodiment of the disclosure.

FIG. 3 is a flow diagram of a method 300 for verifying the interference fit of a fastener 206 in accordance with an embodiment of the disclosure. The method 300 is illustrated as a collection of operations in a logical flow chart, which represents a sequence of operations that can be implemented in hardware, software, or a combination thereof. In the context of software, the operational acts generally represent computer readable instructions that, when executed by one or more processors, perform the recited operations. For purposes of discussion, the method 300 is described with reference to the components of the exemplary system 200 described above with reference to FIG. 2.

At 302, the controller 226 activates the shear wave transducer 218 by generating an electronic signal to drive the shear wave transducer 218 with the dynamic wave generator 228. Regardless of the type of the electronic signal, at 304, the shear wave transducer 218 begins transmitting ultrasonic signal 220 through the shear wave couplant media interface into the fastener 206 thereby causing shear waves to propagate through the fastener 206. In some embodiments, a shear wave couplant media interface (for instance, an ultrasonic coupling gel) can be applied to the fastener 206 before 304 to aid in coupling ultrasonic signals to/from the fastener 206. Moreover, the shear wave transducer 218 can be applied to the fastener 206 with a selected force.

The shear wave transducer 218 can be moved about on the end (or the head 208) of the fastener 206 while it transmits the ultrasonic signal 220 into the fastener 206. Thus, no matter where within the fastener 206 that the regions 222 (which experience stress arising from the interference fit) happen to occur, the shear wave transducer 218 will likely sense the stress caused by the interference fit. Moreover, should the stress arising from the interference fit vary within the fastener 206, the shear wave transducer 218 will likely sense the full range of that variation. Indeed, in some situations, it might be beneficial to select a particular distance from the longitudinal center of the fastener 206, place the shear wave transducer 218 at that distance from the center, and move the shear wave transducer in a generally circular motion about the head of the fastener 206 to sense the interference fit around the fastener 206 at that radial distance.

For instance, should the fastener 206 or the hole be out-of-round, it might happen that portions of the circumference of the shank experience more or less of an interference fit than other portions of the circumference. As a result of such variations, a range of readings might be obtained for any given fastener 206. Depending on the desires of the user, the minimum, maximum, average, or other values within the range may be used to determine the degree of the interference fit. For instance, if any portion of the range indicates an out-of-specification fit the fastener 206 may be determined to be out-of-specification. In such situations, the fastener 206 could be removed, re-installed, replaced (with another fastener 206 of the same or a different size), etc.

As the transmitted ultrasonic signal 220 travels through the fastener 206, the stressed regions 222 mode-convert a portion of the transmitted ultrasonic signal 220 to longitudinal waves. The non-mode converted shear component and the mode-converted longitudinal component of the transmitted ultrasonic signal 220 return to the shear wave transducer 218 whereupon the shear wave transducer 218 receives the return ultrasonic signal 224 at 306.

At 308, the controller 226 correlates the return ultrasonic signal 224 with the degree of interference fit between the fastener 206 and the materials 202 and 204. For instance, in some embodiments, the controller 226 determines the amplitude or energy of the mode-converted longitudinal component of the return ultrasonic signal 224. In some embodiments, the controller 226 determines the amplitude or energy of the non-mode converted shear component of the return ultrasonic signal 224. In some embodiments, the controller 226 determines both amplitudes or energies and a product and a ratio of the two amplitudes or energies. In addition, or in the alternative, the controller 226 can integrate the longitudinal and/or shear components to determine the amount of energy returned in the respective components and to correlate the same to the degree of the interference fit. In this regard, it is sometimes helpful to couple the shear waves (of the transmitted and/or return ultrasonic signals 220 and 224) into/from the fastener 206 and shear wave transducer 218 using an acoustic coupling material.

Regardless of which value(s) the controller 226 determines from the return ultrasonic signal 224, the controller 226 correlates the value(s) to a degree of the interference fit between the fastener 206 and the materials 202 and 204. In doing so, the controller 226 can take into account various factors such as the type of fastener 206, the length of the fastener, the diameter (or other dimension) of the fastener 206, whether the fastener 206 has a head 208 and (if so) what type of head 208 the fastener 206 has, the types of material(s) 202 and 204, the material of the fastener 206 itself, whether the fastener 206 is installed at an angle (other than 90 degrees) with respect to the surface(s) of the materials 202 and 204, etc. For instance, where the fastener 206 has a head 208, it may be the case that the interaction of the material 202 or 204 abutting the head 208 and the head 208 might cause a region of the shank 210 and the head 208 to experience some tensile/compressive stress. This stress might influence the mode conversion of the transmitted ultrasonic signal 220. Thus, by considering experimentally obtained data correlating such factors and the degree of the interference fit, the controller 226 can determine the degree of the interference fit being experienced by the fastener 206 and the materials 202 and 204, as indicated at 308.

Figure 4:
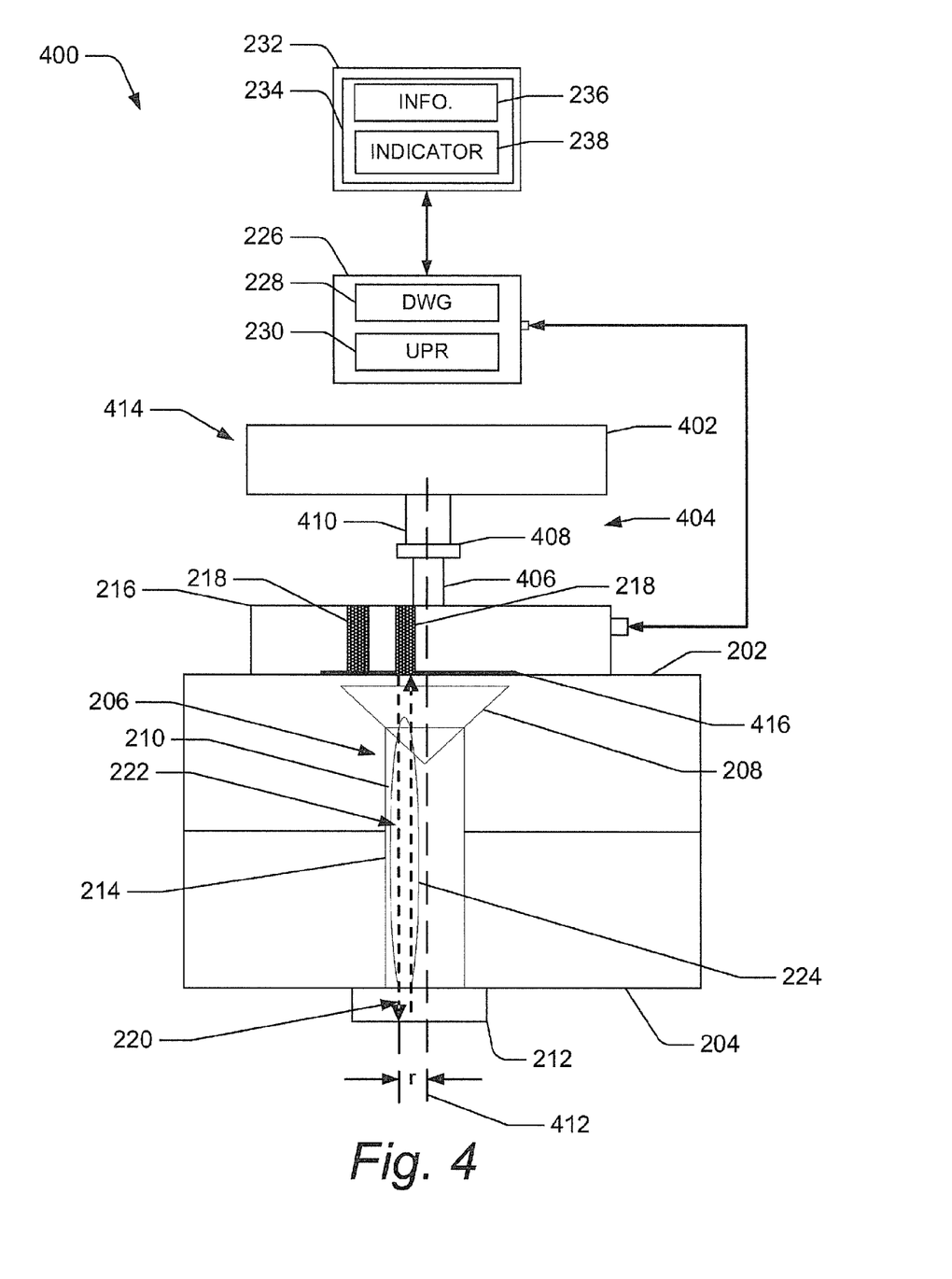
FIG. 4 is a cross-sectional view of another apparatus configured to verify the interference fit of a fastener in accordance with an embodiment of the disclosure.

FIG. 4 is a cross-sectional view of another apparatus configured to verify the interference fit of a fastener in accordance with an embodiment of the disclosure. A system 400 includes similar hardware, software etc. as that illustrated in the system 200 in FIG. 2. However, the configuration of some of the hardware, software, etc. in system 400 differs from that in the system 200, as described is disclosed herein.

The system 400 of FIG. 4 includes a rail 402 to which the IFF probe 216 mounts. The length and shape of the rail 402 allows it to roughly position the IFF probe 216 over or adjacent to fasteners 206 installed in various work pieces such as, but not limited to, the fuselage 102, the wing assemblies 104, tail assembly 106, etc of the aircraft 100 of FIG. 1. In some embodiments, the rail 402 includes features selected to orient the shear wave transducer 218 to deliver approximately 0 degree shear waves into the fastener 206 at specific locations on the fastener head, although it has been found that even shear wave transducers 218 oriented by hand provide sufficiently accurate and repeatable results for many applications. With continuing reference to FIG. 4, the rail 402 also includes vernier positioning instruments (not shown) for aligning the shear wave transducer 218 with the fastener 206. These vernier positioning instruments allow the probe 216 to align the shear wave transducer 218 with the fastener 206 such that the transmitted ultrasonic signal 220 travels just within the fastener 206 and along its surface where the regions 222 of compressive stress arising from the interference fit are likely found. In some embodiments, the probe 216 includes an adapter shaped and dimensioned to mate with the head 208 of the fastener 206 and to align the shear wave transducer 218 accordingly. While some embodiments provide vernier control of the alignment of the shear wave transducer 218 and the fastener 206, it has been found that even hand-positioning the shear wave transducer 218 adjacent the fastener 206 produces satisfactory results for many applications.

Nonetheless, the shear wave transducer 218 can be positioned over the fastener 206 and aligned with its longitudinal axis 412 (or center). In some embodiments, the shear wave transducer 218 is a ring transducer dimensioned so that the active cells of the shear wave transducer 218 point toward and through the regions 222 within the fastener 206 subject to compressive force due to interference fits which the fastener 206 might be experiencing. Thus, the active elements of the shear wave transducer 218 can be located a distance r from the longitudinal axis 412 of the fastener 206. In some embodiments, the distance r is selected so that the active elements of the shear wave transducer align with an annular column within the fastener 206 that the surface of the fastener 206, the distance r, and the geometry of the active elements of the shear wave transducer 218 define.

In addition, or in the alternative, the system 400 includes a force assembly 404 operably coupling the rail 402 and the IFF probe 216. The force assembly 404 illustrated by FIG. 4 includes a jack, or spring force actuator apparatus 406, vacuum assembly (see FIG. 8), or other mechanism for holding the shear wave transducer 218 against the fastener 206 (or material 202 or 204 should the fastener 206 be covered with such material). The force assembly 404 can also include a screw 408, lever, or other mechanism operably coupled to the transducer fixture assembly 406 to adjust the force with which the transducer fixture assembly 406 holds the shear wave transducer 218 against the fastener 206. FIG. 4 also illustrates that the force assembly 404 can include a load cell 410, scale, or other force measuring device operably coupled between the rail 402 and the transducer fixture assembly 406 in such a manner that the load cell 410 measures the force with which the transducer fixture assembly 406 holds the shear wave transducer 218 against the fastener 206. Moreover, the screw 408 and the load cell 410 are communicatively coupled to the controller 226 so that the controller 226 can control the screw 408 (and the transducer fixture assembly 406) and obtain the force as sensed by the load cell 410. Thus, in some embodiments, the controller 226 controls the force with which the shear wave transducer 218 is applied to the fastener 206.

Thus, the rail 402 and force assembly 404 (or, together, a fixture 414) allow the shear wave transducer 218 to be aligned with the fastener 206 and to be applied thereto with a selected force. In addition, or in the alternative, the system 400 includes a layer of gap filler 416, adhesive, or other acoustic coupling material applied between the shear wave transducer 218 and the material 202 or 204. As a result, the shear wave transducer 218 can be acoustically coupled to the fastener 206 for efficient, repeatable, and accurate transmission of ultrasonic signals to the fastener 206 (as well as for the reception of return ultrasonic signals 224 there from).

Figure 5:
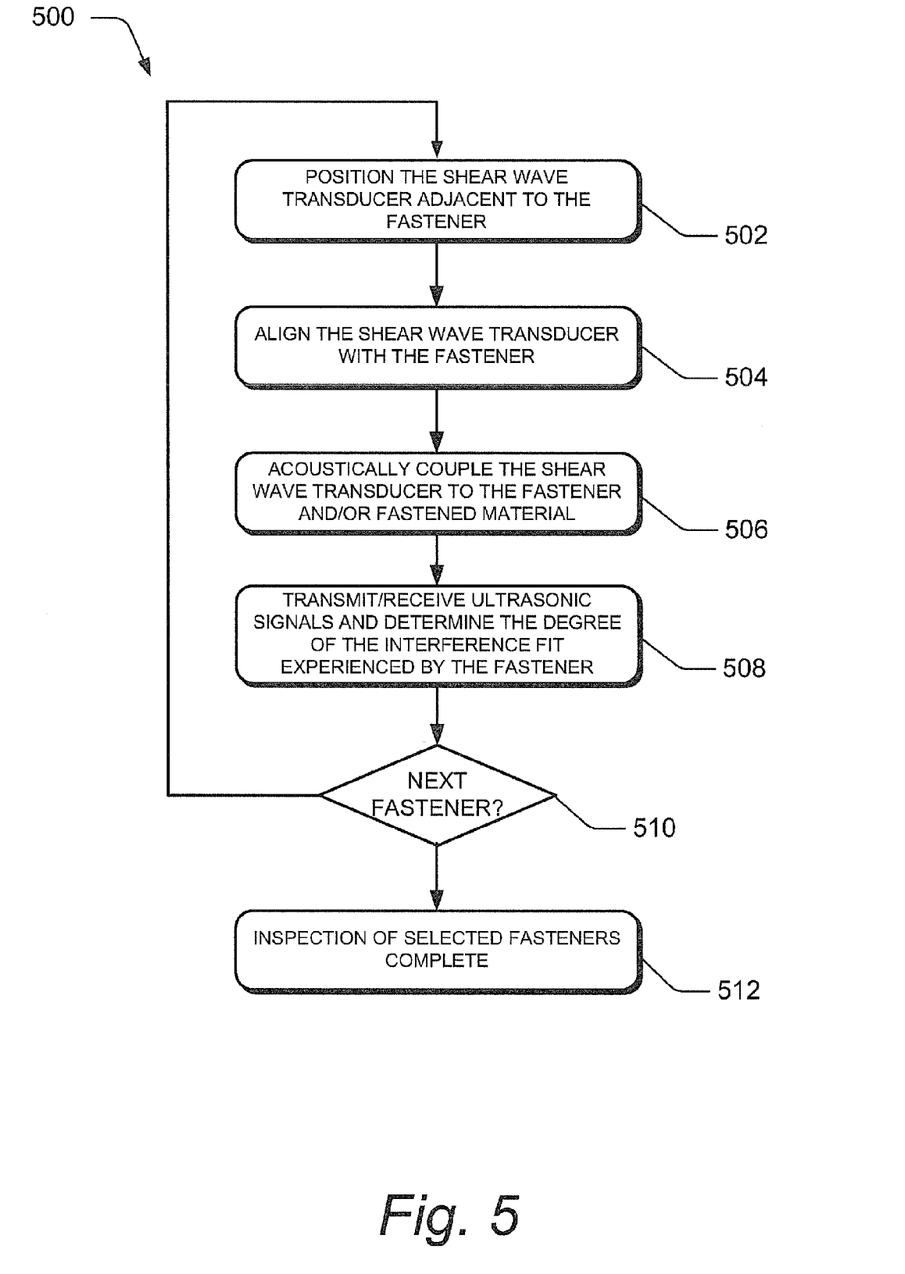
FIG. 5 is a flow diagram of another process for verifying the interference fit of a fastener in accordance with an embodiment of the disclosure.

FIG. 5 is a flow diagram of another method 500 for verifying the interference fit of a fastener 206 in accordance with an embodiment of the disclosure. In preparation for method 500 the acoustic coupling material 414 may be applied to one or more fasteners 206. For instance, a thin film of the acoustic coupling materials 414 may be applied to a line (or group) of fasteners 206 on a wing assembly 104 (see FIG. 1). Should one of the materials 202 or 204 cover the fastener(s) 206, the acoustic coupling material can be applied to the covering material 202 or 204.

In some embodiments, controller 226 uses positioning mechanisms operably coupled to the rail 402 and the IFF probe 216 to position the IFF probe 216 near one of the fasteners 206. See 502. Some embodiments of the rail 402 include vernier positioning mechanisms to precisely position the IFF probe 216 on the fastener 206 to couple the ultrasonic shear waves into specific locations chosen to provide accurate interference fit measurements.

At 504, the controller 226 aligns the shear wave transducer 218 with the fastener 206. More particularly, the shear wave transducer 218 can be aligned with the fastener 206 such that the active elements of the shear wave transducer 218 point into the regions 222 subject to compressive forces arising from interference fits between the fastener 206 and the materials 202 and 204. The alignment may be accomplished via the controller 226 and the positioning mechanisms (vernier or otherwise) on the rail 402. More particularly, the controller 226 can access CAD/CAM (Computer Aided Design/Computer Aided Manufacturer) files associated with the aircraft 100 (see FIG. 1) to position the IFF probe 216 in precise relationship with the fastener 206. In addition, or in the alternative, the alignment can be accomplished entirely or partially through the use of an adaptor on the IFF probe 216. That adapter can be shaped and dimensioned to mate with the head of the fastener 206 and to align the shear wave transducer accordingly. Thus, at 506, the active elements of the shear wave transducer are aligned to transmit the ultrasonic signal 220 through the length of the fastener 206 and along its surface.

At 506 the transducer fixture assembly 406 and screw 408 (or vacuum system of FIG. 8, spring loading mechanism, or other apparatus) of the force assembly 404 are controlled to apply the shear wave transducer 218 to the fastener 206 with a force selected to correspond to the configuration of the particular fastener 206. That force helps spread the acoustic coupling material 414, fill any gaps between the shear wave transducer 218 and the fastener 206, and thereby provide acoustic coupling between the shear wave transducer 218 and the fastener 206.

As explain elsewhere herein, the degree of the interference fit between the fastener 206 and the materials 202 and 204 is determined. See 508. For instance, the ultrasonic signal 220 can be transmitted into the fastener 206, travel along the surface of the fastener 206, and be mode-converted in correspondence to the degree of the interference fit being experienced by the fastener 206. Thus, at 508, the controller 226 receives the return ultrasonic signal 224, analyzes the same, and determines the degree of the interference fit being experience by the fastener 206.

At 510, the shear wave transducer can be withdrawn from the fastener 206 and re-positioned adjacent to another fastener 206 to determine the degree of the interference fit between that other fastener 206 and the materials 202 and 204.

Otherwise if it is so desired, at 512, the inspection of the fastener(s) 206 can be considered complete.

FIGS. 6A-H illustrate the interference fit of a number of data samples in accordance with an embodiment of the disclosure. Charts 600A, 600B, 600E, and 600F show the energy (volt-msec) of the longitudinal and shear wave components of the reflected signal versus degree of IFF from wave forms received during testing. The charts 600A-600H include a number of test data samples, each having a known interference fit. A nonlinear or non-linear slope (volt-msec/interference fit) is measured for each test data sample using embodiments of methods and apparatus in accordance with the teachings of the present disclosure. Moreover, the probe 216 used to obtain the test data samples was spring loaded to hold the shear wave transducer 218 against the fastener 206 with a constant selected force.

A regression analysis correlation process may be used to establish a correlation curve between the wave form characteristics and the interference fit with the materials 202 and 204. For each of the type of measurement illustrated by the charts 600A-600H, a threshold range may be determined for respective interference fits that are within design requirements, thus calibrating the systems 200 and 400 of FIGS. 2 and 4. For example, these correlations may include correlating empirical (or test) data with the measured degree of interference fit. In such an instance, the degree of the interference fit may be known for a number of test samples. The test samples may be analyzed using the techniques and/or apparatus described herein to measure changes between the transmitted ultrasonic signal 220 and the return ultrasonic signal 224. The measured changes may then be plotted, associated, or otherwise correlated with the corresponding interference fit of the known sample. In other instances, simulation data may be used with the measured stresses or an analytical expression may be derived from empirical and/or simulation data. In addition, or alternatively, a look-up table may be created to convert a measurement from a signal analysis into a corresponding interference fit.

Each type of fastener material may have a unique correlation between the observed stresses and the interference fit. For example, a reinforced composite material may have a first associated look-up table (or analytical expression, etc.) while a metallic material may have a second associated look-up table. In addition, different variations of reinforced composite materials may include unique look-up tables to establish the associated corresponding interference fit from a signal analysis. Similarly, various correlations between the materials 202 and 204 and various fastener 206 types and sizes may be performed to improve the results of the analyses disclosed herein.

To test a fastener 206, the correlation process described above may be reversed once the threshold range is established. Thus, instead of testing a known interference fit with an unknown correlated return ultrasonic signal 224, the process may include testing an unknown interference fit using a known correlated return ultrasonic signal 224.

In the experimental system used to obtain the data samples a Ritec RPR-4000 high power tone burst pulse/receiver was used as the ultrasonic pulse receiver 230. Moreover, the dynamic wave generator 228 was set to drive the ultrasonic pulse receiver 230 with a wave with an amplitude of 500 volts. It was also found that the dynamic wave generator 228 could drive the ultrasonic pulse receiver 230 with signals as low as 100 volts (and even 50 volts in some cases) with meaningful results being generated by the controller 226. The experimental system used a Dell 630 laptop computer configured with PicoScope 6 software and LabView version 8.0 software (with MatLab capabilities) as the controller 226. Additionally, the Dell 630 computer was supplemented with a Pico Scope model 5024 USB Digital Oscilloscope. The experimental system was used with Olympus, NDT/Panametric Model Nos. V-155RM and V156RM and Technicsonic 5 MHZ shear wave transducers 218.

Figure 6A:
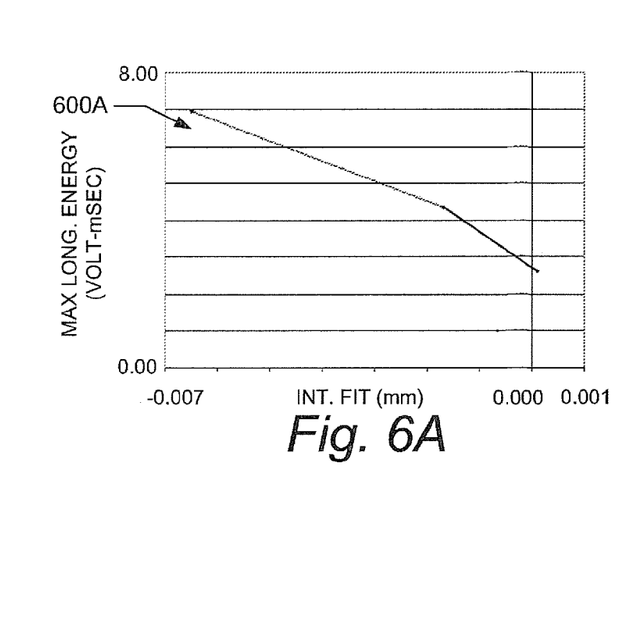
FIG. 6A is a chart of the maximum energy of the longitudinal component of a return ultrasonic signal versus degree of interference fit.

With continuing reference to FIGS. 6A-6H, the charts 600A-600H illustrate the following types of experimental data (or results):

Chart 600A: The maximum energy of the longitudinal component of a return ultrasonic signal 224.

Figure 6B:
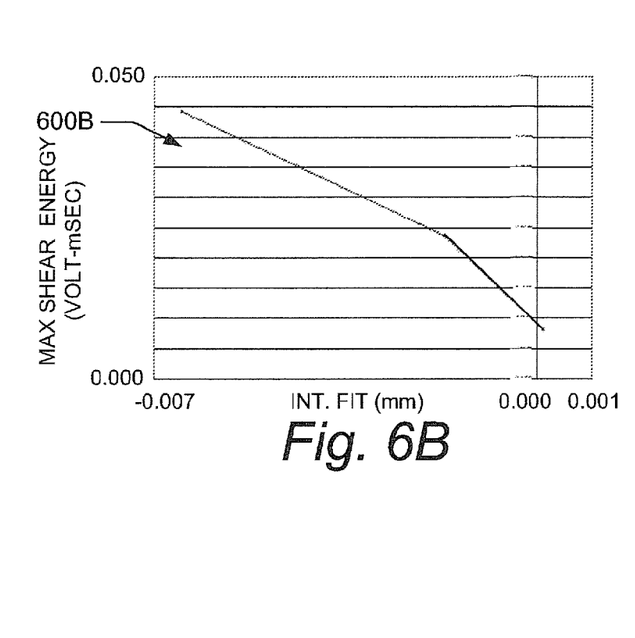
FIG. 6B is a chart of the maximum energy of the shear component of the return ultrasonic signal versus degree of interference fit.

Chart 600B: The maximum energy of the shear component of the return ultrasonic signal 224.

Figure 6C:
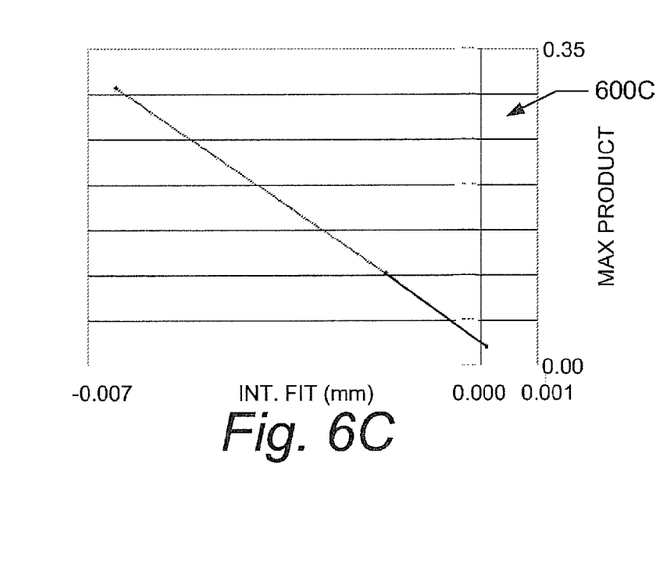
FIG. 6C is a chart of the dot product of the maximum energy of the longitudinal and shear components of the return ultrasonic signal versus degree of interference fit.

Chart 600C: The dot product of the maximum energy of the longitudinal and shear components of the return ultrasonic signal 224.

Figure 6D:
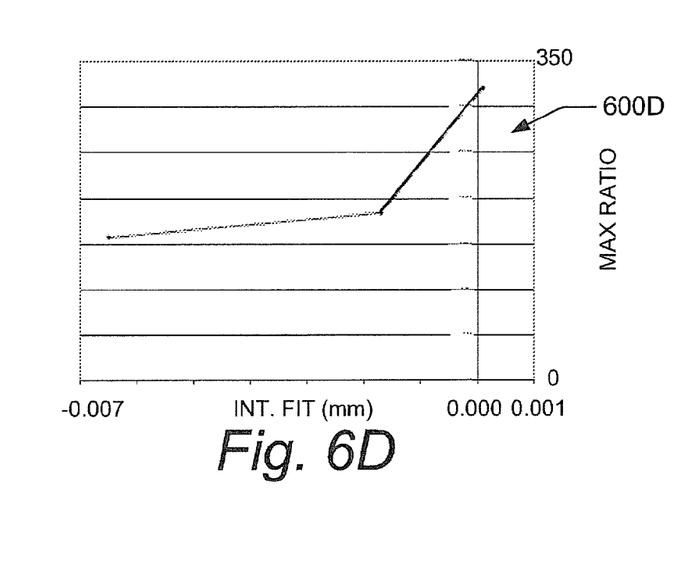
FIG. 6D is a chart of the ratio of the maximum energy of the longitudinal and shear components of the return ultrasonic signal versus degree of interference fit.

Chart 600D: The ratio of the maximum energy of the longitudinal and shear components of the return ultrasonic signal 224.

Figure 6E:
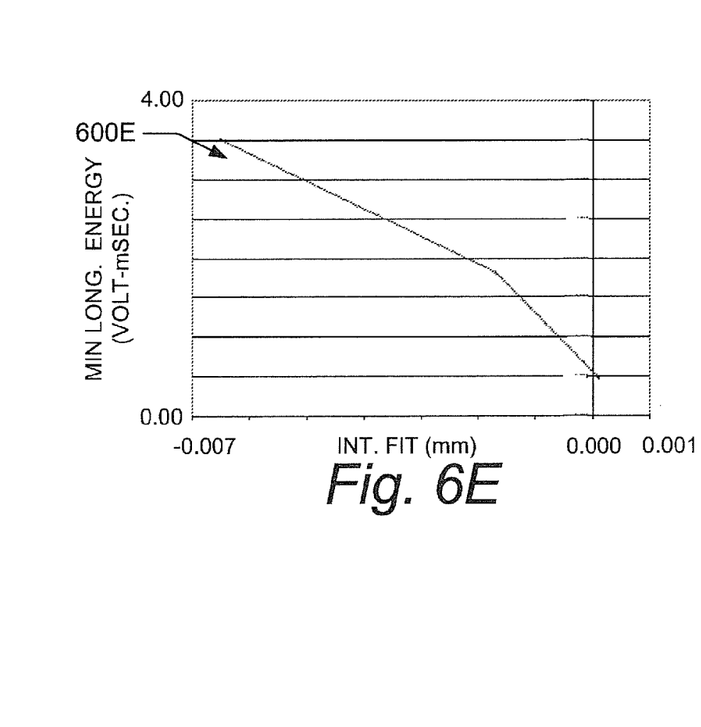
FIG. 6E is a chart of the minimum energy of the longitudinal component of the return ultrasonic signal versus degree of interference fit.

Chart 600E: The minimum energy of the longitudinal component of the return ultrasonic signal 224.

Figure 6F:
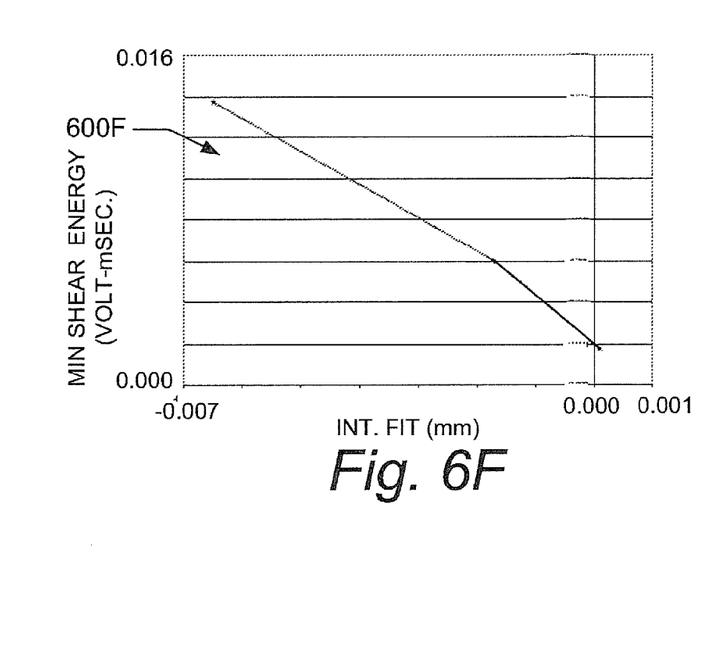
FIG. 6F is a chart of the minimum energy of the shear component of the return ultrasonic signal versus degree of interference fit.

Chart 600F: The minimum energy of the shear component of the return ultrasonic signal 224.

Figure 6G:
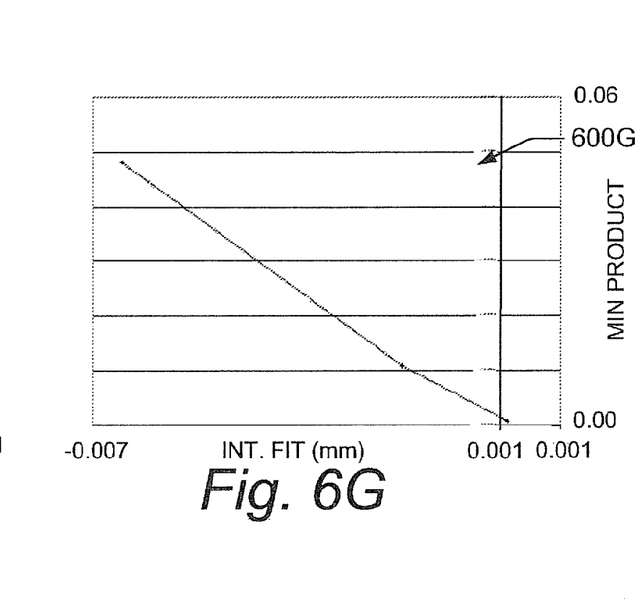
FIG. 6G is a chart of the dot product of the minimum energy of the longitudinal and shear components of the return ultrasonic signal versus degree of interference fit.

Chart 600G: The dot product of the minimum energy of the longitudinal and shear components of the return ultrasonic signal 224.

Figure 6H:
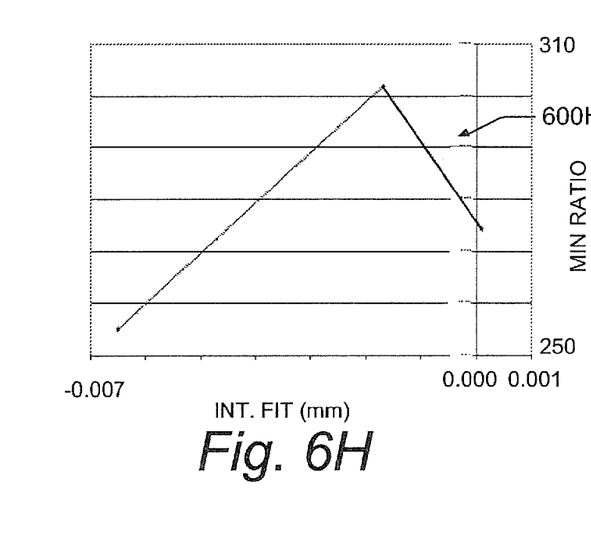
FIG. 6H is a chart of the ratio of the minimum energy of the longitudinal and shear components of the return ultrasonic signal versus degree of interference fit.

Chart 600H: The ratio of the minimum energy of the longitudinal and shear components of the return ultrasonic signal 224.

The charts 600A-H illustrate that the energy of the longitudinal and shear wave components of the return ultrasonic signal 224 (charts 600A, 600B, 600E, and 600F) and the dot product thereof (charts 600C and 600G) exhibit better correlation with the degree of the interference fit than the ratio of these values (charts 600D and 600H). Accordingly, in some embodiments, the energy of the longitudinal and shear wave components of the return ultrasonic signal 224 and/or the dot products thereof are used to determine the degree of the interference fit between various fasteners 206 and the fastener holes 214. Moreover, the degree of various interference fits can be determined without removing the fasteners 206. Thus, fastener installation verifications can be conducted more rapidly, more efficiently, and with greater accuracy and precision than heretofore possible.

Figure 7:
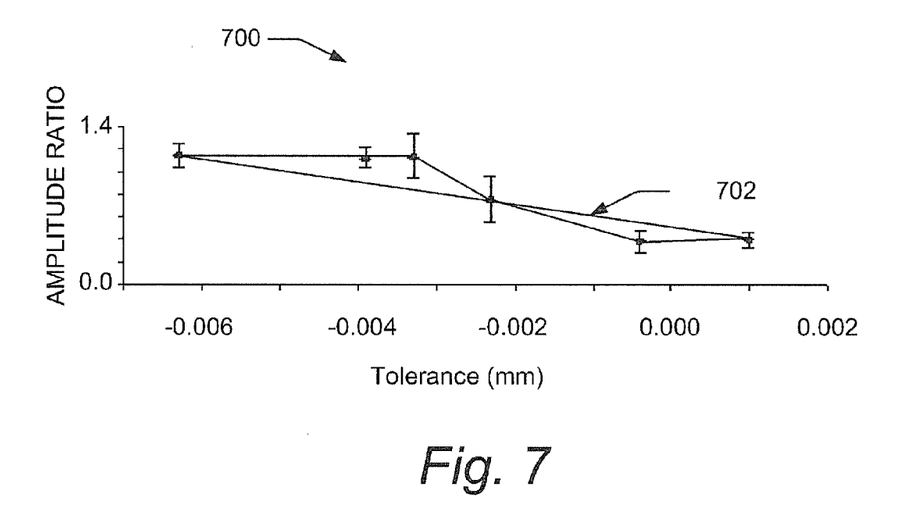
FIG. 7 is a chart illustrating the interference fit of a number of data samples in accordance with an embodiment of the disclosure.

FIG. 7 illustrates a chart 700 of experimental data (ratios of the longitudinal and shear wave components of the return ultrasonic signal 224) gathered for a particular small fastener 206 across a range of interference fits. The chart indicates, for each data point, the maximum and minimum ratios of the longitudinal and shear wave energy (sensed as the shear wave transducer 218 was moved about the head 208 of the fastener 206). The chart 700 also indicates the average ratios for each of the known interference fits tested. The interference fits (the values along the x-axis) represent the differences in fit up diameters between the shank 210 of the fastener 206 and the fastener holes 214. It might be useful to note that the 0.001 mm positive interference fit and the 0.0005 mm (the two right most data points) negative interference fit test setups were out of tolerance (i.e., the interference fit was too loose) for the particular fastener 206 under consideration. As illustrated by FIG. 7, a least squares fit, regression techniques, etc. can be applied to the data to determine a linear or non-linear relationship 702 between the amplitude ratios and the degree of interference fit. Since the ratios illustrated by FIG. 7 demonstrate a generally linear relationship and since the two out-of-tolerance data points have ratios laying generally below the other data points, chart 700 also illustrates that the ratio between the longitudinal and shear components of the return ultrasonic signal 224 can be used in at least some situations to determine whether the fastener 206 and the fastener hole 214 provide a satisfactory interference fit.

Furthermore, a demonstration conducted on a test setup of a Boeing 787 wingbox resulted in the following data.

TABLE 1

Boeing 787 Wingbox Test Data

| Fit Type | Trial No | Long Amp. (mV) | Shear Amp. (mV) | Ratio (dB) |
|---|---|---|---|---|
| No Interference | 4 | 116 | 170 | −3.31982 |
| No Interference | 3 | 71 | 100 | −2.97483 |
| Interference | 2 | 136 | 98 | 2.846257 |
| Interference | 1 | 238 | 104 | 7.190872 |

Thus, Table 1 also illustrates that the ratio between the longitudinal and shear components of the return ultrasonic signal 224 can be used to determine whether a fastener 206 is experiencing an interference fit with the fastener hole 214 in which it is installed.

Figure 8:
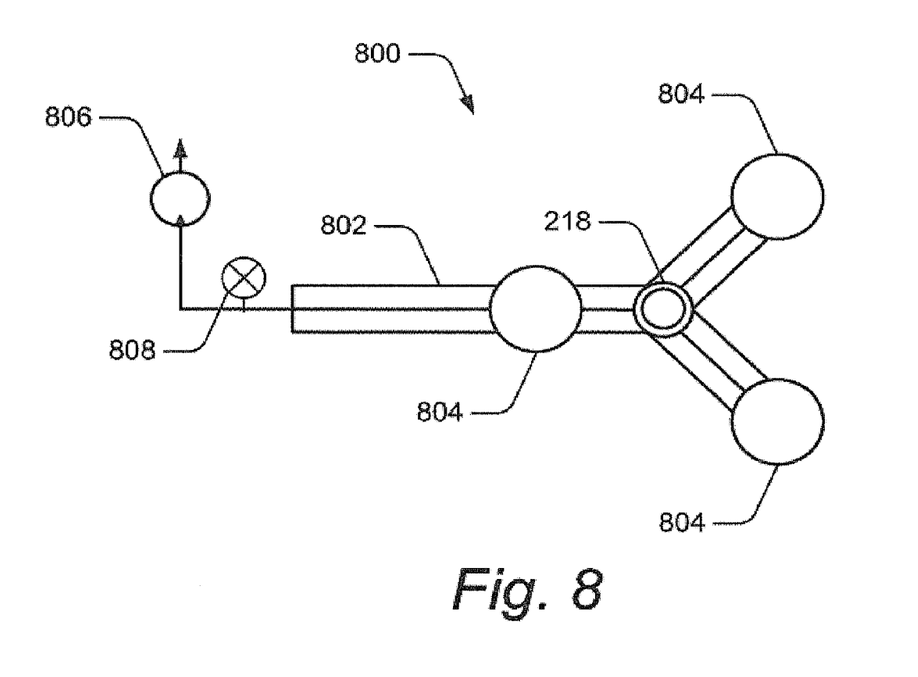
FIG. 8 is a schematic diagram illustrating an interference fit probe in accordance with an embodiment of the disclosure.

FIG. 8 is a schematic diagram illustrating a fastener interference fit (IFF) probe 800 in accordance with an embodiment of the disclosure. The IFF probe 800 includes one or more shear wave transducers 218 and a frame 802 maintaining the shear wave transducer 218 in fixed relationship with a triad of vacuum cups 804. The vacuum cups 804 communicate with a vacuum pump 806 and a control valve (not shown) such that when a vacuum is applied to the vacuum cups 804, the probe 800 pulls the shear wave transducer 218 against the fastener 206 with a force determined by the vacuum pressure, the ambient pressure, and the effective surface area of the vacuum cups 804. In some embodiments, the controller 226 communicates with a pressure transducer 808 and controls the vacuum pump and associated control valve to determine the force with which the shear wave transducer 218 is applied to the fastener 206.

While preferred and alternate embodiments of the disclosure have been illustrated and described, as noted above, many changes can be made without departing from the spirit and scope of the disclosure. Accordingly, the scope of the disclosure is not limited by the disclosure of these preferred and alternate embodiments. Instead, the disclosure should be determined entirely by reference to the claims that follow.

What is claimed is:

1. A system comprising:
   an ultrasonic transducer;
   a processor in communication with the ultrasonic transducer; and
   a memory in communication with the processor and storing computer readable instructions which when executed by the processor cause the processor to perform operations, the operations comprising:
   transmitting a shear wave ultrasonic signal via the ultrasonic transducer, wherein when the ultrasonic transducer is aligned with a fastener through a shear wave propagating gel couplant interface, the ultrasonic transducer transmits the shear wave ultrasonic signal through a region of the fastener subject to stress when the fastener experiences an interference fit;
   receiving, via the ultrasonic transducer and when the ultrasonic transducer is aligned with the fastener, a return ultrasonic signal from the fastener, the return ultrasonic signal having undergone a mode conversion while traveling through the region subject to stress and corresponding to a degree of interference fit which the fastener is experiencing;
   determining, from the mode conversion of the return ultrasonic signal, the degree of interference fit which the fastener is experiencing; and
   outputting an indication of the degree of the interference fit.

2. The system of claim 1, wherein determining the degree of interference includes comparing a first amount of energy of a longitudinal wave component and a second amount of energy of a shear wave component of the return ultrasonic signal.

3. The system of claim 1, wherein the interference fit is between the fastener and a material selected from the group consisting of a metallic material and a composite material.

4. The system of claim 1, wherein the return ultrasonic signal is reflected from an end surface of a shank of the fastener.

5. The system of claim 1, further comprising a display including a graphical user interface including an indicator to indicate a go/no-condition of the fastener based on the degree of the interference fit.

6. The system of claim 1, further comprising a fixture to align the ultrasonic transducer and the fastener.

7. The system of claim 1, further comprising a fixture to apply the ultrasonic transducer to the fastener with a selected force.

8. The system of claim 1, further comprising a shear wave propagating gel couplant through which the shear wave ultrasonic signal is propagated from the transducer and into the fastener, and through which the return ultrasonic signal is transmitted from the fastener to the transducer.

9. The system of claim 1, further comprising a rail on which the ultrasonic transducer is movably mounted.

10. A non-transitory computer readable storage medium storing computer readable instructions which when executed by a processor cause the processor to perform operations, the operations comprising:
    transmitting a shear wave ultrasonic signal via an ultrasonic transducer, wherein when the ultrasonic transducer is aligned with a fastener, the ultrasonic transducer transmits the shear wave ultrasonic signal through a region of the fastener subject to stress when the fastener experiences an interference fit;
    receiving, via the ultrasonic transducer and when the ultrasonic transducer is aligned with the fastener, a return ultrasonic signal from the fastener, the return ultrasonic signal having undergone a mode conversion while traveling through the region subject to stress and corresponding to a degree of interference fit which the fastener is experiencing;
    determining, from the mode conversion of the return ultrasonic signal, the degree of interference fit which the fastener is experiencing; and
    outputting an indication of the degree of the interference fit.

11. The non-transitory computer readable storage medium of claim 10, wherein determining the degree of interference fit includes determining a ratio of a first amplitude of a mode converted component of the return ultrasonic signal to a second amplitude of a non-mode converted component of the return ultrasonic signal.

12. The non-transitory computer readable storage medium of claim 10, wherein determining the degree of interference fit includes comparing a first amount of energy of a longitudinal wave component and a second amount of energy of a shear wave component of the return ultrasonic signal.

13. The non-transitory computer readable storage medium of claim 10, wherein the interference fit is between the fastener and a material selected from the group consisting of a metallic material and a composite material.

14. The non-transitory computer readable storage medium of claim 10, wherein the return ultrasonic signal is reflected from an end surface of a shank of the fastener.

15. The non-transitory computer readable storage medium of claim 10, wherein the operations further include displaying a graphical user interface including an indicator to indicate a go/no-condition of the fastener based on the degree of the interference fit.

16. The non-transitory computer readable storage medium of claim 10, wherein a fixture aligns the ultrasonic transducer and the fastener.

17. The non-transitory computer readable storage medium of claim 10, wherein a fixture applies the ultrasonic transducer to the fastener with a selected force.

18. The non-transitory computer readable storage medium of claim 10, wherein the shear wave ultrasonic signal is propagated through a shear wave propagating gel couplant from the transducer and into the fastener, and through which the return ultrasonic signal is transmitted from the fastener to the transducer.

19. The non-transitory computer readable storage medium of claim 10, wherein the ultrasonic transducer is movably mounted on a rail.

20. The system of claim 1, wherein determining the degree of interference fit includes determining a ratio of a first amplitude of a mode converted component of the return ultrasonic signal to a second amplitude of a non-mode converted component of the return ultrasonic signal.

* * * * *